United States Patent [19]

Bannai et al.

[11] 4,237,125

[45] Dec. 2, 1980

[54] 1α-HYDROXY-24-DEHYDROVITAMIN D₃ PHARMACEUTICAL COMPOSITIONS AND USES THEREOF

[75] Inventors: Kiyoshi Bannai; Norio Ohnuma; Seiichi Ishizuka, all of Hino; Junji Kubo, Hachioji; Tatuyuki Naruchi, Hino, all of Japan

[73] Assignee: Teijin Limited, Osaka, Japan

[21] Appl. No.: 906,785

[22] Filed: May 17, 1978

[30] Foreign Application Priority Data

May 24, 1977 [JP] Japan .................................. 52-59454

[51] Int. Cl.³ .......................... A61K 51/39; C07J 9/00
[52] U.S. Cl. ................................. 424/236; 260/397.2
[58] Field of Search ...................... 424/236; 260/397.2

[56] References Cited

U.S. PATENT DOCUMENTS

| | | | |
|---|---|---|---|
| 3,846,455 | 11/1974 | Ikekawa et al. | 260/397.2 |
| 3,879,548 | 4/1975 | De Luca et al. | 424/236 |
| 3,928,397 | 12/1975 | Ikekawa et al. | 260/397.2 |
| 4,022,891 | 5/1977 | Takeshita et al. | 424/236 |
| 4,069,321 | 1/1978 | Jones et al. | 260/397.2 |

OTHER PUBLICATIONS

Tetrahedron Letters, 13, pp. 1107–1108, (1977), Onisko et al.

Fed. of European Biochemical Society Letters, 76, pp. 177–181, (1977), Ikekawa et al.

*Primary Examiner*—Douglas W. Robinson
*Attorney, Agent, or Firm*—Sherman & Shalloway

[57] ABSTRACT

Novel 1α-hydroxy-24-dehydrovitamin D₃ and its hydroxyl-protected derivatives; novel 1α-hydroxy-24-dehydroprevitamin D₃ and its hydroxyl-protected derivatives; and novel 1α,3β-dihydroxycholesta-5,7,24-triene or its hydroxyl-protected derivatives which are key intermediates for preparing the aforesaid compounds. Novel processes for preparing these compounds are also provided. 1α-Hydroxy-24-dehydrovitamin D₃ has a pharmacological action of controlling the calcium metabolism of warm-blooded animals, and is useful as a prophylactic or therapeutic pharmaceutical for vitamin D deficient disease and related diseases.

7 Claims, No Drawings

1α-HYDROXY-24-DEHYDROVITAMIN D₃, PHARMACEUTICAL COMPOSITIONS AND USES THEREOF

This invention relates to novel 1α-hydroxy-24-dehydrovitamin $D_3$ (1α-OH-$\Delta^{24}$-$D_3$) and its derivatives resulting from the protection of its hydroxyl groups which are expressed by the following formula

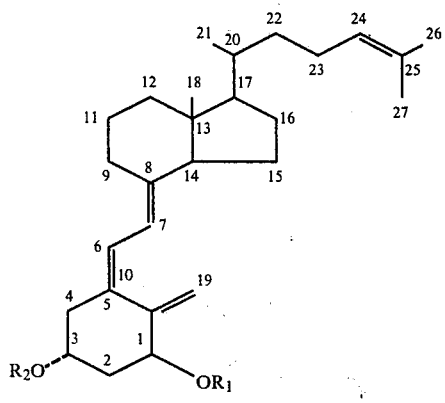

wherein $R_1$ and $R_2$ are identical or different, and each represent a hydrogen atom or a protective group for the hydroxyl groups at the 1- and 3-positions which can be split off.

The invention also relates to novel 1α-hydroxy-24-dehydroprevitamin $D_3$ (1α-OH-$\Delta^{24}$-pre $D_3$), an isomer of the 1α-OH-$\Delta^{24}$-$D_3$, and its derivatives resulting from the protection of its hydroxyl groups, which are expressed by the following formula

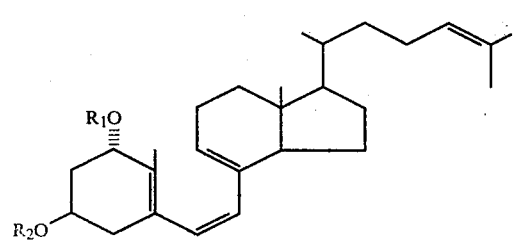

wherein $R_1$ and $R_2$ are identical or different, and each represent a hydrogen atom or a protective group for the hydroxyl groups at the 1- and 3-positions which can be split off.

The invention also relates to novel 1α,3β-dihydroxy-cholesta-5,7,24-triene [1α,3β-(OH)₂-cholestatriene] or its derivatives resulting from the protection of its hydroxyl groups, which are key intermediates for the preparation of the 1α-OH-$\Delta^{24}$-$D_3$ and 1α-OH-$\Delta^{24}$-preD₃ and their hydroxylprotected derivatives, and which are expressed by the following formula

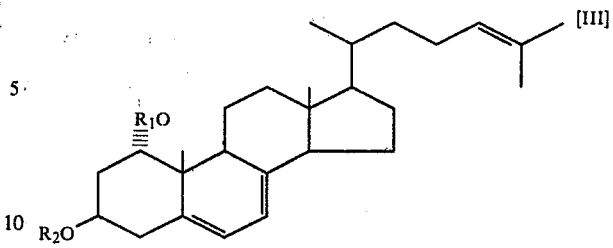

wherein $R_1$ and $R_2$ are identical or different, and each represent a hydrogen atom or a protective group for the hydroxyl groups at the 1- and 3-positions which can be split off.

The invention also relates to novel processes for preparing the 1α-OH-$\Delta^{24}$-$D_3$, 1α-OH-$\Delta^{24}$-preD₃, 1α-3β-(OH)₂-cholestatriene and their hydroxyl-protected derivatives.

The invention further relates to a pharmaceutically effective composition for warm-blooded animals, especially a pharmaceutical composition for controlling calcium metabolism of warm-blooded animals, which comprises the 1α-OH-$\Delta^{24}$-$D_3$ as an active ingredient.

24-Dehydrovitamin $D_3$ of the following formula

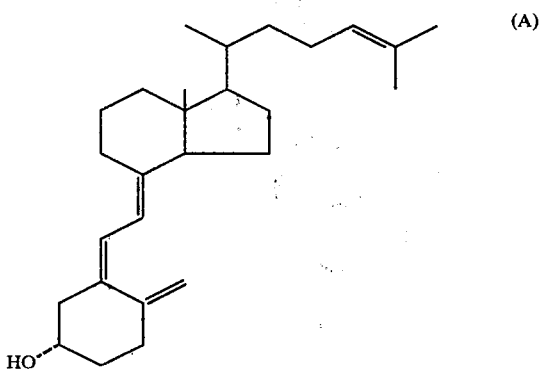

is known to have a similar structure to the novel 1α-OH-$\Delta^{24}$-$D_3$ of the present invention (Tetrahedron Letters No. 13, pages 1107–1108, 1977). However, no pharmacological property of the 24-dehydrovitamin $D_3$ has been reported.

The 1α,3β-(CH)₂-cholestatriene, 1α-OH-$\Delta^{24}$-preD₃, 1α-OH-$\Delta^{24}$-$D_3$ and their hydroxyl-protected derivatives can be produced, for example, by the procedure shown in Reaction Scheme 1 below.

Reaction Scheme 1

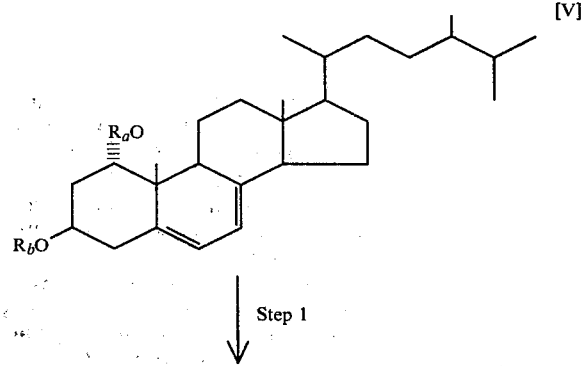

Step 1

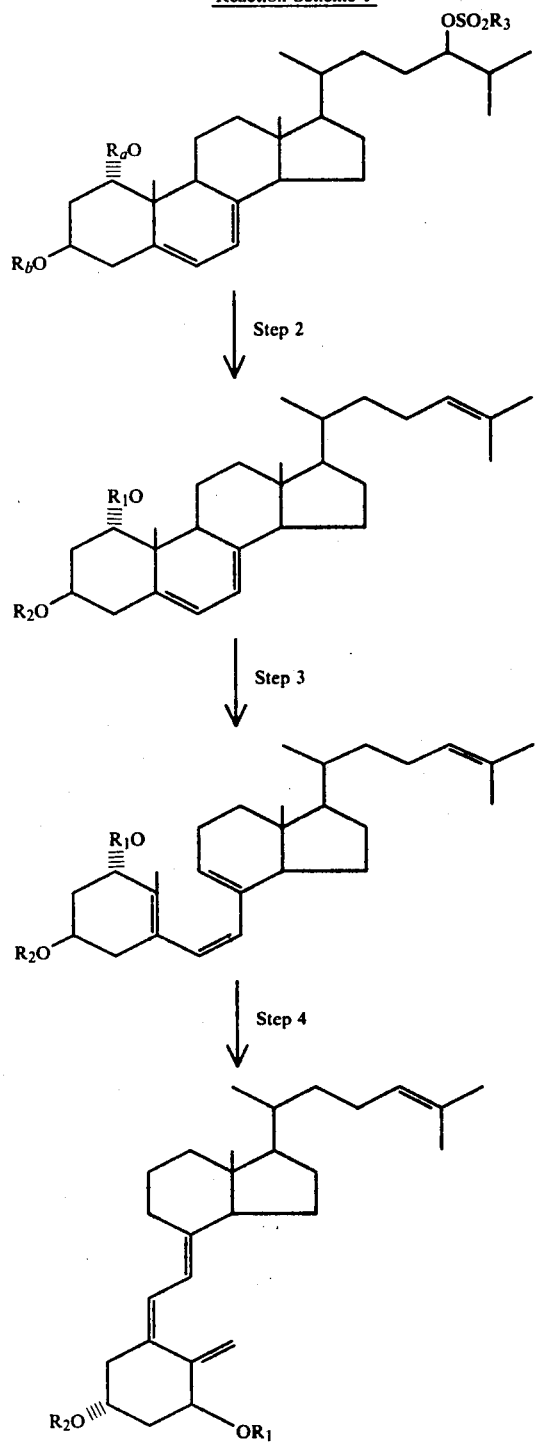

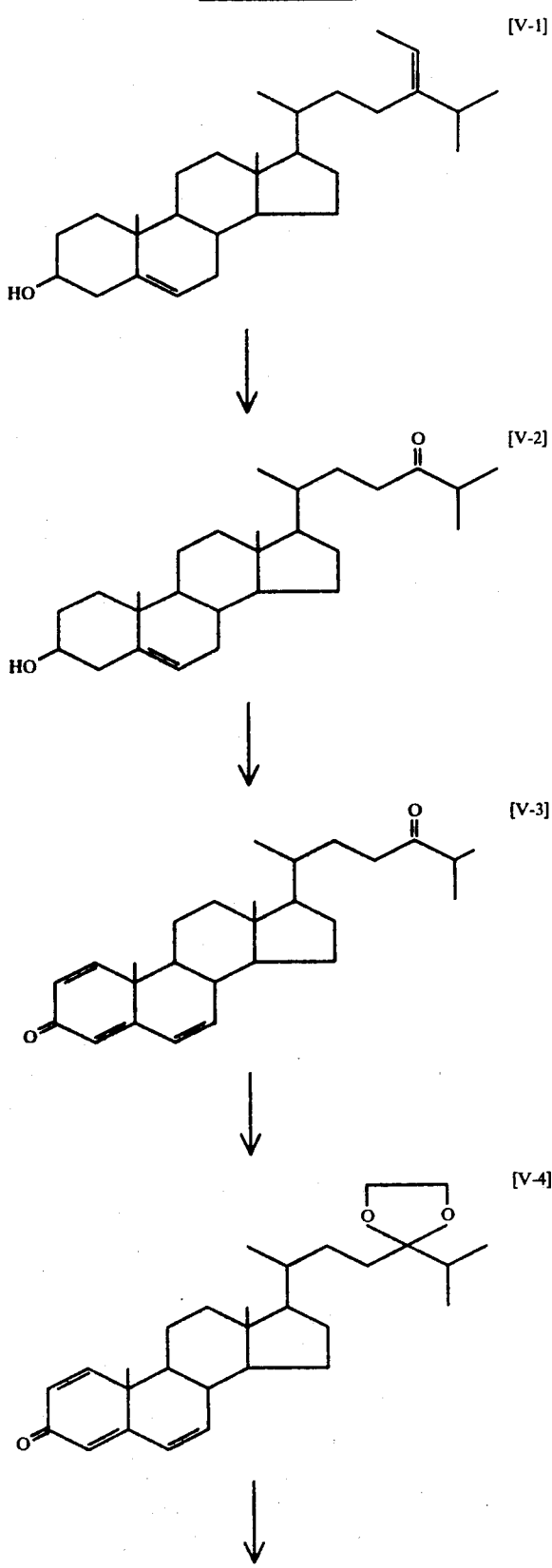

process schematically shown below in Reaction Scheme 2.

In the above Reaction Scheme, $R_a$ and $R_b$ are identical or different, and each represent a hydroxyl-protective group capable of being split off; $R_1$ and $R_2$ are identical or different, and each represent a hydroxyl-protective group capable of being split off; and $R_3$ represents a monovalent hydrocarbon radical optionally substituted by an inert substituent.

The $1\alpha,3\beta$-diprotected hydroxy-24-hydroxycholesta-5,7-diene of formula [V] in Reaction Scheme 1 can be prepared easily, for example by the process described in U.S. Pat. No. 4,022,891. It can also be produced by the -continued
Reaction Scheme 2

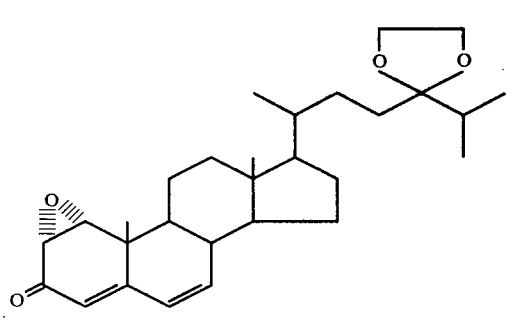
[V-5]

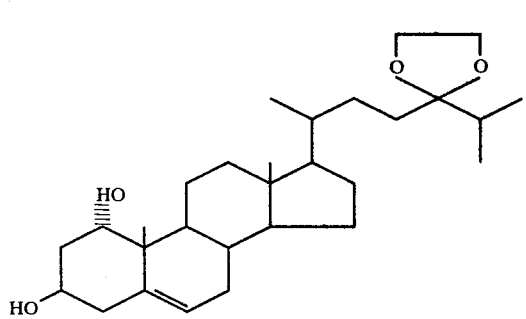
[V-6]

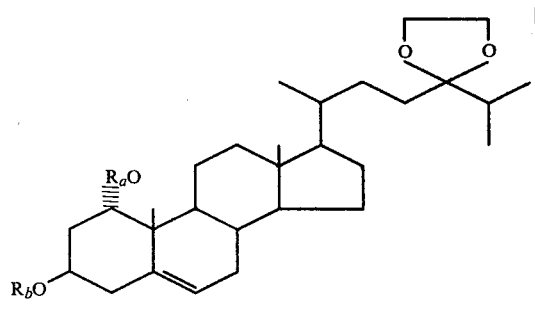
[V-7]

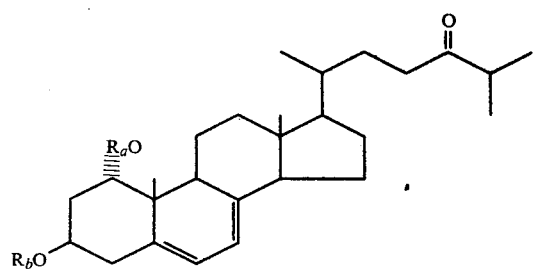
[V-8]

-continued
Reaction Scheme 2

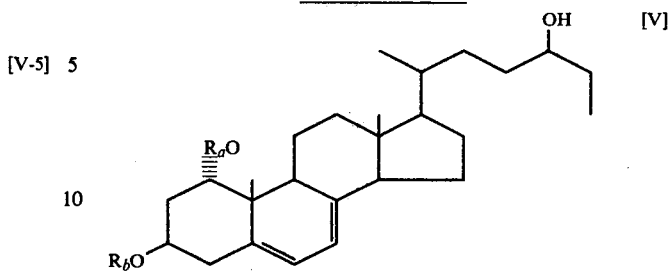
[V]

In Reaction Scheme 2, $R_a$ and $R_b$ are the same or different, and each represent a hydroxyl-protective group capable of being split off.

The steps of the process shown in Reaction Scheme 1 will be described in detail below.

Step 1

As shown in Reaction Scheme 1, a 1α,3β,24-trihydroxycholesta-5,7-diene derivative of the formula

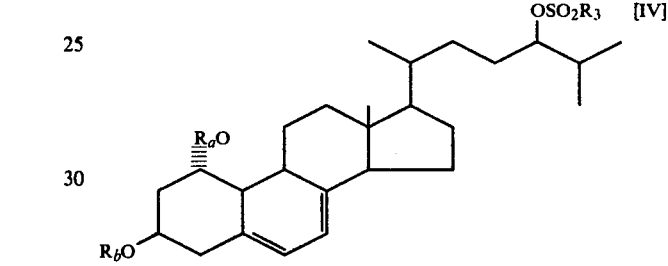
[IV]

wherein $R_a$ and $R_b$ are identical or different, and each represent a hydroxyl-protective group capable of being split off, and $R_3$ represents a monovalent hydrocarbon group optionally substituted by an inert substituent.

is produced by reacting a 1α,3β-diprotected hydroxy-24-hydrocholesta-5,7-diene of the formula

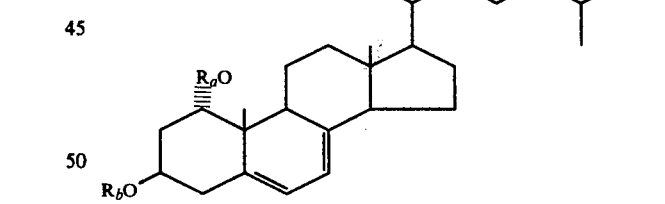
[V]

wherein $R_a$ and $R_b$ are as defined above, with an organic sulfonyl halide of the formula $$XSO_2R_3 \qquad [VI]$$

wherein $R_3$ is as defined above, and X represents a halogen atom, in the presence of an organic or inorganic base, for example pyridine, collidine, triethylamine, N,N-dimethylaniline, sodium amide, an alkali metal or alkaline earth metal hydroxide, carbonate or bicarbonate, or an alkali metal alkoxide.

The reaction of Step 1 may be carried out using an organic base of the type exemplified above (e.g., pyridine, collidine, triethylamine or N,N-dimethylaniline) as a solvent. Or it may be carried out in the presence of the aforesaid organic or inorganic base in an aprotic organic solvent such as dimethyl formamide, dimethyl sulfoxide, hexamethyl phosphoramide, methylene chloride, chloroform or benzene. The reaction temperature is, for example, $-30°$ C. to $60°$ C., and temperatures of $-20°$ C. to $30°$ C. are especially suitable.

In formula [VI] representing the organic sulfonyl halide, $R_3$ may be any monovalent hydrocarbon group optionally substituted by an inert substituent. Suitable $R_3$ groups include, for example, alkyl groups containing 1 to 6 carbon atoms, aryl groups containing 6 to 9 carbon atoms such as a phenyl, tolyl, xylyl, ethylphenyl or propylphenyl group, and aralkyl groups such as a benzyl or phenethyl group. X is preferably a chlorine atom.

Step 2

In this step, the $1\alpha,3\beta,24$-trihydroxycholesta-5,7-diene derivative of formula [IV] produced in Step 1 is desulfonated, and as required, the hydroxyl-protective groups are split off, to afford a $1\alpha,3\beta$-dihydroxycholesta-5,7,24-triene or its hydroxyl-protected derivative expressed by the formula

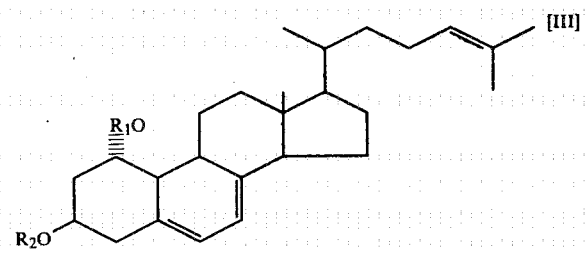

wherein $R_1$ and $R_2$ are identical or different, and each represent a hydrogen atom or a hydroxylprotective group capable of being split off.

The desulfonation in Step 2 is carried out essentially by heating only. Preferably, the desulfonation reaction is carried out in the same solvent as described above with regard to Step 1 in the presence of the same organic or inorganic base as described above with regard to Step 1. In Step 2, an organic base such as pyridine, collidine, triethylamine or N,N-dimethylaniline can be used as the solvent, as is the case with Step 1.

The desulfonation reaction in Step 2 can be carried out at a temperature of $30°$ to $180°$ C. If a higher temperature within this range is used, the rate of desulfonation becomes faster correspondingly. If the reaction temperature is too high, however, side-reactions occur. The preferred temperature range is therefore from $80°$ to $140°$ C. Advantageously, the desulfonation reaction is carried out in an atmosphere of an inert gas such as a nitrogen gas or argon gas.

The reaction of Step 1 and the reaction of Step 2 can be carried out in the same solvent as stated hereinabove, and the reaction of Step 2 proceeds by heating only. Hence, the reactions of Steps 1 and 2 can be sequentially carried out in the same reactor.

Thus, after the reaction of Step 1, the reaction of Step 2 can be performed by merely raising the temperature of the solvent to a higher temperature suitable for the reaction of Step 2. Needless to say, the base is preferably present in the reaction system of the reaction of Step 2. It is advantageous therefore that the organic or inorganic base is added in Step 1 in an amount in excess of that required as an acceptor for a hydrogen halide such as hydrogen chloride generated as a by-product of the sulfonylation reaction; or that when the base is added in Step 1 in an amount required to act as an acceptor for the hydrogen halide, the base is additionally supplied after the reaction of Step 1 and then the reaction of Step 2 is performed.

In Step 1, it is especially preferred to perform the reaction using the organic base itself as a solvent. On the other hand, it is especially preferred in Step 2 to perform the reaction in an aprotic organic solvent such as dimethyl formamide, dimethyl sulfoxide, or hexamethyl phosphoramide.

The protective groups ($R_a$ and $R_b$) for the hydroxyl groups at the 1- and 3-positions of the $1\alpha,3\beta$-diprotected hydroxy-24-hydroxycholesta-5,7-diene of formula [V], the starting material in Step 1, the protective groups ($R_a$ and $R_b$) for the hydroxyl groups at the 1- and 3-positions in the $1\alpha,3\beta,24$-trihydroxycholesta-5,7-diene derivative of formula [IV], the starting material of Step 2, and the protective groups (i.e., when $R_1$ and $R_2$ represent protective groups $R_a$ and $R_b$) for the hydroxyl groups at the 1- and 3-positions of the $1\alpha,3\beta$-dihydroxycholesta-5,7,24-triene derivative of formula [III], the product of Step 2 may be the same protective groups. These protective groups may be any groups which can be converted to hydroxyl groups without destroying the cholesta-5,7-diene skeleton expressed by formula [V], [IV] or [III].

Since the compounds of formulae [V], [IV] and [III] have two or more unsaturated bonds in their structure, the protective groups are preferably those which can be split off by hydrolysis and converted to hydroxyl groups. Preferred protective groups are carboxylic acid residues and groups which form ether linkages with hydroxyl groups. Examples of the protective groups are listed below.

(1) Carboxylic acid residues:

$C_1$–$C_{12}$ aliphatic or aromatic carboxylic acid residues or their nitro-, halogen- and alkoxy-substituted derivatives, for example, acetyl, propanoyl, butanoyl, pentanoyl, pivaloyl, caproyl, cyclohexanoyl, chloroacetyl, bromoacetyl, benzoyl, p-bromobenzoyl, p-nitrobenzoyl, ethylbenzoyl, and toluyl groups. Of these, acetyl, benzoyl and propanoyl groups are especially preferred.

(2) Groups which form ether linkages with hydroxyl groups:

A tert.-butyl group, a benzyl group, a triarylmethyl group such as a triphenylmethyl group, a tetrahydropyranyl group, a methoxymethyl group, and an alkyl-substituted silyl group such as a trimethylsilyl group. Of the above protective groups, the acyl groups (1) are especially preferred, but the invention is in no way limited to them.

The $1\alpha,3\beta$-dihydroxy-cholesta-5,7,24-triene [$1\alpha,3\beta$-(OH)$_2$-chloestatriene] of formula [III] and its hydroxyl-protected derivatives can be purified, for example, by column chromatography, thin-layer chromatography using silica gel or by recrystallization.

Step 3

In this step, the $1\alpha,3\beta$-dihydroxycholesta-5,7,24-triene [$1\alpha,3\beta$-(OH)$_2$-chloestatriene] or its derivative of formula [III] formed in Step 2 is subjected to the irradiation of ultraviolet light to afford a $1\alpha$-hydroxy-24-dehydroprevitamin $D_3$($1\alpha$-OH-$\Delta^{24}$-pre $D_3$) or its hydroxyl-protected derivative expressed by the following formula

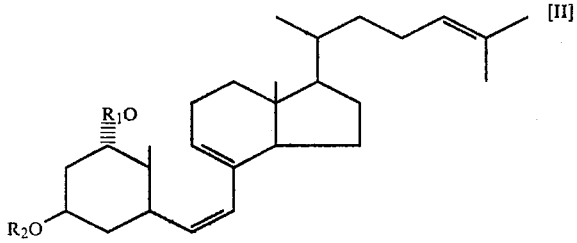

wherein $R_1$ and $R_2$ are identical or different, and each represent a hydroxyl-protective group capable of being split off.

When a hydroxyl-protected derivative of $1\alpha$-hydroxy-24-dehydroprevitamin $D_3$ ($1\alpha$-OH-$\Delta^{24}$-pre $D_3$) expressed by the following formula:

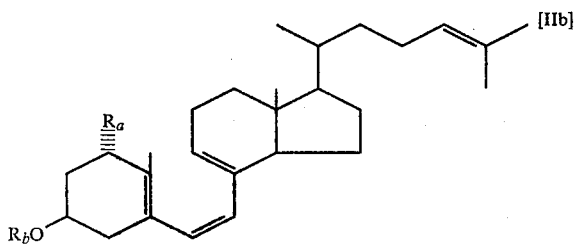

wherein $R_a$ and $R_b$ are identical or different, and each represent a carboxylic acid residue or a group which forms an ether linkage with a hydroxyl group, is formed by the above reaction, it is hydrolyzed to afford $1\alpha$-hydroxy-24-dehydroprevitamin $D_3$ of the following formula

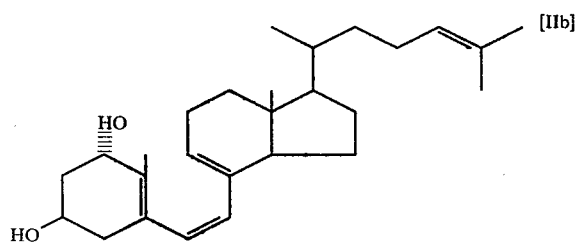

The starting material in the reaction of Step 3 may be any of the $1\alpha,3\beta$-(OH)$_2$-cholestatriene or its derivatives resulting from the protection of its hydroxyl groups at the 1- and 3-positions, where are expressed by formula [III]. Preferably, these compounds formed in the reaction of Step 2 are purified prior to use in Step 3.

The reaction of Step 3 is advantageously carried out by dissolving the preferably purified $1\alpha,3\beta$-(OH)$_2$-cholestatriene or its protected derivatives in an inert organic solvent, and irradiating ultraviolet light onto the solution in an atmosphere of an inert gas at a temperature of $-20°$ C. to $60°$ C., preferably $-10°$ C. to $20°$ C. The irradiating time is 0.5 to 20 minutes, preferably 1 to 10 minutes.

Examples of the inert organic solvent used in this step are hydrocarbons and halogenated hydrocarbons such as hexane, heptane, cyclohexane, ligroin, benzene, toluene, xylene, bromobenzene, chlorobenzene, carbon tetrachloride, 1,2-dichloroethane or 1,2-dibromoethane; ethers such as diethyl ether, tetrahydrofuran, dioxane, methyl cellosolve or phenyl cellosolve; and alcohols such as methanol, ethanol, propanol, hexanol, or cyclohexanol. Benzene, toluene, diethyl ether, methanol, and ethanol, either alone or as mixtures, are particulary preferably used in this invention. If such a solvent is used, the subsequent isomerization reaction to be described can be carried out in the same solvent after ultraviolet irradiation.

The resulting $1\alpha$-OH-$\Delta^{24}$-pre $D_3$ and its protected derivatives can also be purified by column chromatography or thin-layer chromatography using silica gel as in the purification of the product of Step 2.

The protective groups can be split off in a customary manner.

When the protective group of the protected derivative is a carboxylic acid residue, it can be split off by deacylation using a method which comprises decomposing it in an alkali solution of an alcohol such as methanol or ethanol, or a method which comprises reductively decomposing it with LiAlH$_4$, for example, in a solvent such as an ether. Preferably, the deacylation is carried out at a temperature of $-10°$ to $50°$ C.

When the protective group forms an ether linkage with the hydroxyl group, a part of it can be easily removed by reduction or by contact with an acid or alkali.

Step 4

The $1\alpha$-hydroxy-24-dehydroprevitamin $D_3$ ($1\alpha$-OH-$\Delta^{24}$-pre $D_3$) or its protected derivatives expressed by formula [II] is isomerized to $1\alpha$-hydroxy-24-dehydrovitamin $D_3$ ($1\alpha$-OH-$\Delta^{24}$-$D_3$) of the following formula

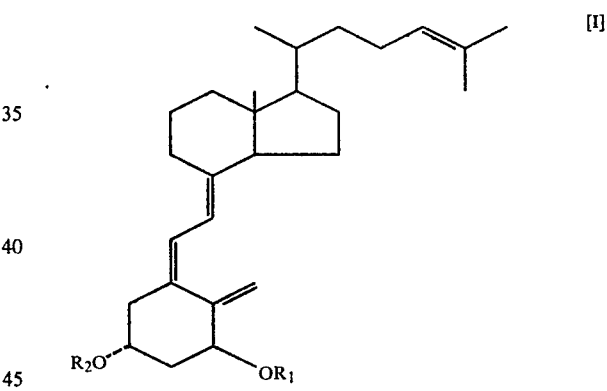

wherein $R_1$ and $R_2$ are identical or different, and each represent a hydrogen atom or a hydroxyl-protective group capable of being split off, by a heat energy.

$1\alpha$-OH-$\Delta^{24}$-pre $D_3$ or its protected derivatives are stable in the solid (crystalline) state, but when dissolved in an inert solvent described in Step 3, are gradually isomerized to $1\alpha$-OH-$\Delta^{24}$-$D_3$ or its protected derivatives of formula [I] even at room temperature or at a lower temperature of, say, $-20°$ C.

However, to perform the isomerization reaction within a relatively short time, it is advantageous to employ a reaction temperature of $10°$ to $150°$ C., preferably $30°$ to $100°$ C. Preferably, the isomerization reaction is carried out in an inert atmosphere.

When a protected derivative of $1\alpha$-OH-$\Delta^{24}$-$D_3$ is formed in Step 4, the protective groups are split off in the same way as described above with regard to Step 3 to form $1\alpha$-OH-$\Delta^{24}$-pre $D_3$.

The $1\alpha$-OH-$\Delta^{24}$-pre $D_3$ or its protected derivative of formula [II] and the $1\alpha$-OH-$\Delta^{24}$-$D_3$ or its protected derivative have an equilibrium relation as shown below.

$1\alpha\text{-OH-}\Delta^{24}\text{-pre D}_3 \rightleftarrows 1\alpha\text{-OH-}\Delta^{24}\text{-D}_3$ This equilibrium relation is shifted more to the right-hand side as the temperature is lower. Hence, as the isomerization temperature in Step 4 is lower, the reaction product is richer in $1\alpha\text{-OH-}\Delta^{24}\text{-D}_3$, but on the other hand, the rate of reaction becomes lower as the isomerization temperature is lower.

It is clear therefore that during the reaction of Step 3 and the subsequent purifying step, a reaction of gradually isomerizing $1\alpha\text{-OH-}\Delta^{24}\text{-pre D}_3$ formed by the reaction of Step 3 to $1\alpha\text{-OH-}\Delta^{24}\text{-D}_3$ takes place.

The isomerization reaction product in Step 4 can be purified, for example, by column chromatography or thin-layer chromatography using silica gel or by recrystallization as described hereinabove. Such a purifying procedure results in the separation of the isomerized $1\alpha\text{-OH-}\Delta^{24}\text{-D}_3$ or its protected derivative from $1\alpha\text{-OH-}\Delta^{24}\text{-pre D}_3$ or its protected derivative.

The resulting $1\alpha\text{-OH-}\Delta^{24}\text{-D}_3$ has a pharmacological action of controlling calcium metabolism of warm-blooded animals, and is very useful for pharmaceutical applications. Furthermore, the $1\alpha\text{-OH-}\Delta^{24}\text{-pre D}_3$ or its protected derivatives are useful not only as a precursor for $1\alpha\text{-OH-}\Delta^{24}\text{-D}_3$, but also as a post-effective compound for controlling calcium metabolism of warm-blooded animals because as stated hereinabove, these compounds are known to be isomerized gradually to active $1\alpha\text{-OH-}\Delta^{24}\text{-D}_3$ even at a considerably low temperature.

The novel $1\alpha,3\beta\text{-(OH)}_2$-cholestatriene or its derivative expressed by formula [III] which is provided by the present invention can be converted to $1\alpha,3\beta,24,25$-tetrahydroxycholesta-5,7-diene or its derivative, which is a key intermediate for $1\alpha,24,25$-trihydroxyvitamin $D_3$, by certain methods, for example a method which comprises oxidizing it with osmium tetraoxide preferably in an approximately equimolar amount in ether at a temperature of about $-20°$ C. to $20°$ C. to form an osmate at the double bond site of $\Delta^{24}$, and reducing it with $NaHSO_3$, etc. in a pyridine-containing water solvent at a temperature of, say, room temperature, or a method which comprises oxidizing it with m-chloroperbenzoic acid preferably in an equimolar amount in a halogenated hydrocarbon such as methylene chloride or chloroform at a temperature of $-78°$ C. to $30°$ C. to form the corresponding 24,25-epoxide, and cleaving the epoxide by using a mineral acid such as hydrochloric acid or perchloric acid as a catalyst in an ether such as tetrahydrofuran or dioxane.

Furthermore, by reducing the corresponding 24,25-epoxide formed in the above manner with lithium aluminum hydride ($LiAlH_4$) in an ether such as tetrahydrofuran, $1\alpha,3\beta,25$-trihydroxycholesta-5,7-diene or its derivative, which is a key intermediate for $1\alpha,25$-dihydroxyvitamin $D_3$, can be obtained.

PHARMACEUTICAL ACTIVITIES

Natural vitamin $D_3$ is known to be metabolized in vivo by the liver to become 25-hydroxyvitamin $D_3$, and then metabolized by the kidneys to become $1\alpha,25$-dihydroxy-vitamin $D_3$ which exhibits activity. The $1\alpha,25$-dihydroxy-vitamin $D_3$ is believed to have an action of promoting calcium absorption from the intestinal tract, bone resorption (dissolving of calcium from the bone tissues) and bone formation (deposition of calcium on the bone tissues).

The $1\alpha\text{-OH-}\Delta^{24}\text{-D}_3$ provided by the present invention is a novel synthesized vitamin $D_3$ analog which has not been found in vivo. As shown hereinabelow in Examples, $1\alpha\text{-OH-}\Delta^{24}\text{-D}_3$ has been compared in pharmacological action with $1\alpha$-hydroxy-vitamin $D_3$ which is rapidly metabolized to active form of $1\alpha,25$-dihydroxyvitamin $D_3$ in vivo and shows an equivalent activity to $1\alpha,25$-dihydroxyvitamin $D_3$. It has been found as shown in Examples that $1\alpha\text{-OH-}\Delta^{24}\text{-D}_3$ has almost the same activity as $1\alpha$-hydroxyvitamin $D_3$ with regard to calcium absorption from the intestinal tract, but its activity on bone resorption is less than 1/5 of that of $1\alpha$-hydroxyvitamin $D_3$. Thus, $1\alpha\text{-OH-}\Delta^{24}\text{-D}_3$ has a specific pharmacological activity and is expected to show different activities from natural vitamin $D_3$ analogs typified by $1\alpha,25$-dihydroxyvitamin $D_3$.

The $1\alpha\text{-OH-}\Delta^{24}\text{-D}_3$ in accordance with this invention can be applied as a specific drug for diseases induced by abnormal calcium metabolism as compared to active forms of vitamin $D_3$ analogs heretofore known.

Suitable dosages in clinical application, based on the results of pharmacological tests, have been found to be about 0.04 to 0.4 $\mu$g per kilogram of the body weight of a warm-blooded animal.

The $1\alpha$-hydroxy-$\Delta^{24}$-$D_3$ in accordance with this invention can be clinically or veterinarily applied to the treatment of abnormal metabolism of calcium and phosphorus caused by hepatic failure, renal failure, gastrointestinal tract failure and parathroid failure, and related bone diseases, such as vitamin D-dependent rickets, renal osteodystrophy, hypoparathyroidism, osteoporosis, osteomalacia, Behcet disease, malabsorption syndrome, hypocalcemia induced by liver cirrhosis, hypocalcemia induced by steatorrhoea, hypocalcemia used by vitamin D-resistant rickets. $1\alpha\text{-OH-}\Delta^{24}\text{-D}_3$ can be used in combination with other calcium metabolism regulating agents. For example, it can be applied to the treatment of Behcet disease in combination with calcitonin.

Suitable routes of administration include oral, buccal and parenteral (intramuscular, subcutaneous, intravenous, and intrarectal). Dosage forms are, for example, compressed tablets, coated tablets, hard or soft elastic gelatin capsules, ethyl alcohol solutions, oil solutions, and aqueous suspensions.

The solvent for the oil solutions may be a vegetable oil such as a corn, cotton seed, coconut, almond or peanut oil, a fish liver oil, or an oily ester such as Polysorbate 80.

For intrarectal administration, the $1\alpha\text{-OH-}\Delta^{24}\text{-D}_3$ may be formed into a pharmaceutical composition containing a suppository base such as cacao butter or other triglycerides. To prolong the shelf life of the pharmaceutical composition, it advantageously includes an antioxidant such as ascorbic acid, butylated hydroxyanisole, or hydroquinone.

Feed compositions for domestic animals which contain the $1\alpha\text{-OH-}\Delta^{24}\text{-D}_3$ of this invention can be used in amounts not causing toxicity for the prevention of hypocalcemia of cows at, or near, the time of delivery, or the prevention of hypocalcemia of domestic animals with no history of hypocalcemia. When such compositions are administered to poultry during oviredeposition, it is possible to prevent them from laying soft-shelled eggs. This constitutes another characteristic feature of the $1\alpha$-hydroxy-$\Delta^{24}$-$D_3$ of this invention.

The following Examples illustrate the present invention in greater detail. It should be noted that these Examples do not in any way limit the scope of the invention.

The test methods used in these Examples for the determination of the characteristics of the products were as follows:

Unless otherwise specified, NMR spectra were determined by Varian EM or JEOL PS/PFT-100 (Nippon Electronics Co., Ltd.) in deuterochloroform (CDCl$_3$) using tetramethylsilane as internal standard.

Mass spectra and high resolution mass spectra were determined by using Shimadzu LKB-900 (Shimadzu Seisakusho Co., Ltd.).

UV spectra were determined by Hitachi EPS-3T (Hitachi Limited) using an ethanol solution.

The melting point was measured by means of a hot stage microscope, and the resulting values were not corrected.

REFERENTIAL EXAMPLE 1

Preparation of 1α,3β-diprotected-24-hydroxycholesta-5,7-diene from cholesterol:

(1) Synthesis of 24-ketocholesterol from fucosterol

Fucosterol was oxidized with ozone and the resulting ozonide was reduced with metallic zinc by the procedure described in U.S. Pat. No. 4,022,891.

(2) Synthesis of cholesta-1,4,6-trien-3,24-dione from 24-ketocholesterol

The 24-ketocholesterol was treated with 2,3-dichloro-5,6-dicyanobenzoquinone by the procedure described in U.S. Pat. No. 4,022,891.

(3) Synthesis of 24,24-ethylenedioxycholesta-1,4,6-trien-3-one from cholesta-1,4,6-trien-3,24-dione 10.2 g of cholesta-1,4,6-trien-3,24-dione was dissolved in 350 ml of dry benzene, and then 70 ml of ethylene glycol was added. Furthermore, 50 mg of p-toluenesulfonic acid was added. The mixture was heated under reflux for 16 hours while removing the generated water as an azeotrope with benzene. After the reaction, the temperature was returned to room temperature, and the reaction mixture was washed with 100 ml of water. The separated aqueous layer was extracted twice with 100 ml of benzene. The benzene layer previously obtained was combined with the extracted benzene layers, and the mixture was washed with 150 ml of a saturated aqueous solution of sodium hydrogen carbonate and then with 150 ml of water. The benzene layer was separated, and dried with sodium sulfate. The solvent was distilled off to afford 10 g of a crude product which had the following characteristics.

UV ($\lambda_{max}^{ethanol}$, nm): 223, 257, 301.

NMR (CDCl$_3$, δ(ppm)): 0.77 (3H, s, 18-CH$_3$), 0.93 (6H, d, J=7Hz, 26,27-(CH$_3$)$_2$), 1.21 (3H, s, 19-CH$_3$), 3.94 (4H, s, ethylene ketal), 5.9–6.4 (4H, m, 2,4,6,7-H$_4$), 7.11 (1H, d, J=10Hz, 1-H).

Mass (m/e): 438 (M$^+$), 395 (M$^{30}$-isopropyl).

From the above characteristics, this product was identified as 24,24-ethylenedioxycholesta-1,4,6-trien-3-one.

(4) Synthesis of 1α,2β-epoxy-24,24-ethylenedioxycholesta-4,6-dien-3-one from 24,24-ethylenedioxycholesta-1,4,6-trien-3-one 6.3 g of 24,24-ethylenedioxycholesta-1,4,6-trien-3-one was dissolved in 225 ml of methanol, and 1.5 ml of a 10% methanol solution of sodium hydroxide was added, and with stirring, 10.8 ml of a 30% aqueous solution of hydrogen peroxide was added. The mixture was stirred at room temperature for 11 hours. After the reaction, the solvent was evaporated under reduced pressure to concentrate the reaction mixture of about 50 ml. 300 ml of water was added, and the mixture was extracted with 200 ml of diethyl ether three times. The diethyl ether layers were combined, and washed successively with water, 1 N hydrochloric acid, a saturated aqueous solution of sodium hydrogen carbonate and then a saturated aqueous solution of sodium chloride, followed by drying with sodium sulfate. The solvent was distilled off to afford 4.0 g of a light yellow residue. The residue was chromatographed on a silica gel column with benzene/ethyl acetate (100/3) as a developing solvent. Recrystallization of the eluate from methanol afforded 3.0 g of while crystals. This product showed the following characteristics.

Melting point (°C.): 149–150.

Elemental analysis: Found: 76.61 (C), 9.35 (H). Calculated: 76.61 (C), 9.31 (H).

NMR (CDCl$_3$, δ(ppm)): 0.77 (3H, s, 18-CH$_3$), 0.92 (6H, d, J=7Hz, 26,27-(CH$_3$)$_2$), 1.18 (3H, s, 19-CH$_3$), 3.42 (1H, dd, J=4Hz, 1.5 Hz, 2β-H), 3.58 (1H, d, J=4Hz, 1⊕-H), 3.93 (4H, s, ethylene ketal), 5.63 (1H, d, J=5Hz, 4-H), 6.07 (2H, s, 6,7H$_2$).

Mass (m/3): 454 (M$^+$), 439 (M$^+$-CH$_3$), 411 (M$^+$-isopropyl), 396 (M$^+$-isopropyl-CH$_3$).

From the above characteristics, this product was identified as 1α,2α-epoxy-24,24-ethylenedioxycholesta-4,6-dien-3-one.

(5) Synthesis of 24,24-ethylenedioxy-1α,3β-dihydroxycholest-5-ene from 1α,2α-epoxy-24,24-ethylenedioxycholesta-4,6-dien-3-one A reactor was filled with 50 ml of dry liquid ammonia and then 1.1 g of a metallic lithium wire cut into bits with a size of 1 to 3 cm was added. The mixture was stirred for 20 minutes while being cooled with dry ice-methanol. A solution of 500 mg of 1α,2α-epoxy-24,24-ethylenedioxycholesta-4,6-dien-3-one in 65 ml of absolute tetrahydrofuran was added dropwise over the course of 50 minutes. The mixture was stirred for 10 minutes, and then the dry ice-methanol bath was removed. The reactor was then immersed in a room temperature methanol bath, and refluxed for 20 minutes with stirring.

Then, the methanol bath was replaced by a dry ice-methanol bath, and the reaction mixture was cooled. 11.7 g of dry ammonium chloride was added in 10 portions over the course of 1 hours with stirring. Then, the dry ice-methanol bath was removed, and the reaction mixture was refuxed for about 2 hours, and allowed to stand overnight with stirring to gasify the ammonia spontaneously and remove it. In the meantime, about 100 ml of water was added, and the mixture was extracted with 100 ml of ethyl acetate three times. The separated organic layers were combined, washed successively with 2 N hydrochloric acid, a saturated aqueous solution of sodium hydrogen carbonate and a saturated aqueous solution of sodium chloride, and dried with sodium sulfate. Distillation of the solvent afforded 490 mg of a pale yellow residue.

The residue was chromatographed on a silica gel column with benzene/ethyl acetate (100/2) as a developing solvent to afford 280 mg of a white product.

Recrystallization of this product from methanol afforded 196 mg of a purified product having the following characteristics.

Melting point (°C.): 164–165.

NMR (CDCl$_3$, δ(ppm)): 0.67 (3H, s, 18-CH$_3$), 0.91 (6H, d, J=7Hz, 26,27-(CH$_3$)$_2$), 1.01 (3H, s, 19-CH$_3$), 3.91 (4H, s, ethylene ketal), 3,7–4.2 (2H, m, 1β,3α-H$_2$), 5.58 (1H, m, 6H).

From the above characteristics, this product was identified as 24,24-ethylenedioxy-1α,3β-dihydroxycholest-5-one.

(6) Synthesis of 1α,3β-diacetoxy-24,24-ethylenedioxycholest-5-ene from 24,24-ethylenedioxy-1α,3β-dihydroxycholest-5-one 3.09 g of 24,24-ethylenedioxy-1α,3β-dihydroxycholest-5-one was dissolved in 30 ml of pyridine, and 15 ml of acetic anhydride was added. The mixture was stirred at 60° C. for 6 hours.

Ice water was added, and the mixture was allowed to stand for 20 minutes, and then extracted with 100 ml of diethyl ether three times. The separated diethyl ether layers were combined, washed successively with 2 N hydrochloric acid, a saturated aqueous solution of sodium hydrogen carbonate, and a saturated aqueous solution of sodium chloride, and dried with sodium sulfate. Distillation of the solvent afforded 3.27 g of a product having the following characteristics.

NMR (CDCl$_3$, δ(ppm)): 0.68 (3H, s, 18-CH$_3$), 0.92 (6H, d, J=6Hz, 26,27-(CH$_3$)$_2$), 1.05 (3H, s, 19CH$_3$), 1.99 and 2.01 (6H, a pair of singlets, 1,3-(CH$_3$CO)$_2$)), 3.95 (4H, s, 24-ethylene ketal), 4.7–5.2 (2H, m, 1β and 3α-H$_2$), 5.50 (1H, m, 6H).

Mass (m/e): 5Cl (M$^+$-isopropyl), 441 (M$^+$-isopropyl-CH$_3$COOH), 424 (M$^+$-2CH$_3$COOH), 381 (M$^+$-isopropyl-2CH$_3$COOH).

From the above characteristics, this product was identified as 1α,3β-diacetoxy-24,24-ethylenedioxycholest-5-one.

(7) Synthesis of 1α,3β-diacetoxycholesta-5,7-dien-24-one from 1α,3β-diacetoxy-24,24-ethylenedioxycholest-5-ene 134 mg of 1α,3β-diacetoxy-24,24-ethylenedioxycholest-5-ene was dissolved in 30 ml of dry hexane, and refluxed vigorously in an atmosphere of an argon gas. During this time, 43.5 mg of 1,3-dibromo-5,5-dimethylhydantoin was added, and the mixture was refluxed with stirring for 30 minutes. The temperature was lowered to room temperature, and the solid was separated by filtration, the solvent was distilled off to obtain a residue.

A mixture of 7 ml of dry p-xylene and 7 ml of scollidine was refluxed with stirring in an atmosphere of argon, and a solution of the above residue in 7 ml of dry xylene was added to the mixture over the course of 10 minutes. The mixture was refluxed with stirring for 10 minutes. At room temperature, the solid was separated by filtration. Water and n-hexane were added to the filtrate, and the mixture was shaken in a separatory funnel. The organic layer was then separated, washed successively with 2 N hydrochloric acid, a saturated aqueous solution of sodium hydrogen carbonate, and a saturated aqueous solution of sodium chloride, and dried with sodium sulfate. The solvent was distilled off to obtain a residue.

The residue was dissolved in 40 ml of acetone, and 25 mg of p-toluenesulfonic acid was added. The mixture was stirred at room temperature for 4 hours. After distilling off a greater portion of the solvent, an aqueous solution of sodium hydrogen carbonate was added, and the mixture was extracted with 70 ml of ethyl acetate three times. The separated ethyl acetate layers were combined, washed with a saturated aqueous solution of sodium chloride, and dried with sodium sulfate. The solvent was distilled off to obtain a residue.

The residue was developed four times with a benzene/acetone (40/1) mixed solvent by chromatography using three silver nitrate-impregnated silica gel thin layers (20 cm×20 cm×0.5 mm) to afford 47 mg of a product having the following characteristics.

UV ($\lambda_{max}^{ethanol}$, nm): 261, 271, 282, 293.

NMR (CDCl$_3$, δ(ppm)): 0.62 (3H, s, 18-CH$_3$), 1.02 (3H, s, 19-CH$_3$), 1.07 (6H, d, J=7Hz, 26, 27-(CH$_3$)$_2$), 2.03 and 2.08 (6H, a pair of singlets, 1,3-(CH$_3$CO)$_2$), 4.7–5.2 (2H, m, 1β and 3α-H$_2$), 5.38, 5.69 (1H, dd, J=2Hz, 6Hz; 1H, d, J=6Hz; 6,7-H$_2$).

Mass (m/e): 498 (M$^+$), 438 (M$^+$-CH$_3$COOH), 422, 378 (M$^+$-2CH$_3$COOH)

From the above characteristics, this product was identified as 1α,3β-diacetoxycholesta-5,7-dien-24-one.

(8) Preparation of 1α,3β-diacetoxy-24-hydroxycholesta-5,7-diene from 1α,3β-diacetoxycholesta-5,7-dien-24-one 119 mg of 1α,3β-diacetoxycholesta-5,7-dien-24-one was dissolved in 12 ml of methanol, and 50 mg of sodium borohydride was added. The mixture was stirred at room temperature for 1 hour. The solvent was distilled off, and 50 ml of ethyl acetate and 30 ml of water were added to the residue. The mixture was shaken in a separatory funnel. The organic layer was separated, and the aqueous layer was extracted with 30 ml of ethyl acetate. The organic layer previously separated was combined with the ethyl acetate layer, and the mixture was washed with 2N hydrochloric acid, a saturated aqueous solution of sodium hydrogen carbonate and a saturated aqueous solution of sodium chloride, and then dried with sodium sulfate. The solvent was distilled off, and 119 mg of a residue was obtained.

The residue was developed with a benzene/acetone (20/1) developing solvent by chromatography using two silica gel thin layers to afford 71 mg of a purified product. The product showed the following characteristics.

UV ($\lambda_{max}^{ethanol}$, nm): 261, 271, 282, 293.

NMR (CDCl$_3$, δ(ppm)): 0.68 (3H, s, 18-CH$_3$), 0.92 (6H, d, J=6Hz, 2,27-(CH$_3$)$_2$), 1.01 (3H, s, 19-CH$_3$), 2.03, 2.08 (6H, s, 1.3-(CH$_3$CO)$_2$), 3.32 (1H, m, 24-H), 4.7–5.2 (2H, m, 1β and 3β-H$_2$), 5.38, 5.69 (1H, dd, J=2Hz, 6Hz; 1H, d, J=6Hz, 6.7-H$_2$).

Mass (m/e): 500 (M$^+$), 482 (M$^+$-H$_2$O), 440 (M$^+$-CH$_3$COOH), 380 (M$^+$-2CH$_3$COOH).

From the above characteristics, this product was identified as 1α,3β-diacetoxy-24-hydroxycholesta-5,7-diene.

REFERENTIAL EXAMPLE 2

Synthesis of 1α,3β-diacetoxy-24-hydroxycholesta-5,7-diene by the partial hydrolysis of 1α,3β,24-triacetoxycholesta-5,7-diene:

54 mg of 1α,3β,24-triacetoxycholesta-5,7-diene was dissolved in 1 ml of tetrahydrofuran, and 1 ml of a cold 1% methanol solution of potassium hydroxide was added. The mixture was allowed to stand overnight in a refrigerator. 30 ml of water was added, and the mixture was extracted with 30 ml of ethyl acetate three times. The separated ethyl acetate layers were combined, washed with dilute hydrochloric acid, a saturated aqueous solution of sodium hydrogen carbonate, and then with water, and dried with anhydrous sodium sulfate. The solvent was distilled off to afford 48 mg of a residue. The resulting residue was chromatographed on a thin layer of silica gel using a benzene/acetone (10/1) developing solvent to afford 7 mg of 1α,3β-diacetoxy-24-hydroxycholesta-5,7-diene having the characteristics shown in Referential Example 1, (8).

EXAMPLE 1

Preparation of 5,7,24-triene by Steps 1 and 2:

20 mg of 1α,3β-diacetoxy-24-hydroxycholesta-5,7-diene was dissolved in 0.5 ml of dry pyridine. To the solution was added 50 μe of methanesulfonyl chloride, and the mixture was allowed to stand overnight at $-20°$ C. The temperature was then returned to room temperature. Water was added, and the mixture was extracted with ether. The ether layer separated was washed successively with dilute hydrochloric acid, a saturated aqueous solution of sodium hydrogen carbonate and water, and dried with anhydrous sodium sulfate. The solvent was distilled off to obtain 22 mg of a residue.

All of the resulting 1α,3β-diacetoxy-24-methanesulfoxycholesta-5,7-diene was dissolved in 0.3 ml of hexamethylphosphoramide, and the inside atmosphere of the reactor was replaced by an argon gas. The solution was stirred at 110° C. ( the temperature of the bath) for 3 hours.

Water was then added to the reaction mixture, and the mixture was extracted with ethyl acetate. The separated ethyl acetate layer was washed successively with dilute hydrochloric acid, a saturated aqueous solution of sodium hydrogen carbonate and water, and dried over anhydrous sodium sulfate. The solvent was then distilled off. The resulting residue was chromatographed on a thin layer of silica gel using a benzene/acetone (30/1) developing solvent to afford 8 ml of a product having the following characteristics. UV ($\lambda_{max}^{ethanol}$, nm): 261, 271, 282, 293.

NMR (CDCl$_3$, δ(ppm)): 0.63 (3H, s, 18-CH$_3$), 1.02 (3H, s, 19-CH$_3$), 1.60, 1.67 (6H, a pair of bs, 26,27-(CH$_3$)$_2$), 2.03, 2.08 (6H, a pair of s, 1,3-(CH$_3$CO)$_2$), 4.7–5.4 (3H, m, 1β,3α,24-H$_3$), 5.38, 5.69 (1H, dd, J=2Hz, 6Hz; 1H, d, J=6Hz, 6.7-H$_2$).

Mass (m/e): 482 (M$^+$), 422 (M$^+$-CH$_3$COOH), 398, 362 (M$^+$-2CH$_3$COOH).

High resolution mass spectrum: Found=482.3389. Require, M$^+$(C$_{31}$H$_{46}$O$_4$)=482.3396.

From the above characteristics, the resulting product was identified as 1α,3β-diacetoxycholesta-5,7-24-triene.

EXAMPLE 2

Preparation of 1α-OH-Δ$^{24}$-D$_3$ by Steps 3 and 4:

8 mg of 1α,3β-diacetoxycholesta-5,7-triene was dissolved in a mixture of 100 ml of benzene and 40 ml of ethyl alcohol.

The solution was placed in an ordinary photoreaction apparatus consisting of a reactor having a lamp provided at its center. The lamp used was a medium-pressure mercury lamp equipped with a Vicor filter (200 W). While the exterior of the reactor was cooled with ice, the inside atmosphere of the reactor was replaced by an argon gas. The solution was exposed to ultraviolet irradiation for 2.5 minutes. At this time, the inside of the reactor attained a temperature of 14° C.

After the reaction, the reaction mixture was transferred to an eggplant-shaped flask, and refluxed for 2 hours in an atmosphere of argon. Then, the solvent was distilled off, and 10 ml of a 2% methanol solution of potassium hydroxide was added. The mixture was stirred, and allowed to stand overnight at room temperature.

On the next day, methanol was distilled off, and water was added. The mixture was extracted with ethyl ether. The ether layer separated was washed successively with dilute hydrochloric acid, a saturated aqueous solution of sodium hydrogen carbonate and water, and dried with anhydrous sodium sulfate. The solvent was distilled off.

The resulting residue was chromatographed on a thin layer of silica gel impregnated with silver nitrate using a benzene/acetone (5/1) developing solvent to afford 1.1 mg of a purified product having the following characteristics.

UV ($\lambda_{max}^{ethanol}$, nm): 264.

NMR (CDCl$_3$, δ(ppm)): 0.54 (3H, s, 18-CH$_3$), 0.93 (3H, d, J=5Hz, 21-CH$_3$), 1.60, 1.67 (6H, bs, 26,27-(CH$_3$)$_2$), 4.23 and 4.43 (2H, m, 1,3-H$_2$), 5.00 and 5.32 (2H, a pair of bs, 19-CH$_2$), 5.09 (1H, bt, J=7Hz, 24-H), 6.00 and 6.38 (2H, a pair of d, J=11Hz, 6,7-H$_2$).

Mass (m/e): 398 (M$^+$), 380 (M$^+$-H$_2$O), 362 (M$^+$-2H$_2$O).

High resolution mass spectrum: Found=398.3182. Require, M$^+$(C$_{27}$H$_{42}$O$_2$)=398.3185.

From the above characteristics, the resulting product was identified as 1α-hydroxy-24-dehydrovitamin D$_3$.

EXAMPLE 3

Preparation of 1α-OH-Δ$^{24}$-D$_3$ diacetate by Steps 3 and 4:

3.5 mg of 1α,3β-diacetoxycholesta-5,7,24-triene was dissolved in a mixture of 100 ml of benzene and 40 ml of ethyl alcohol.

The solution was placed in an ordinary photoreaction apparatus consisting of a reactor having a lamp provided at its center. The lamp used was a medium-pressure mercury lamp equipped with a Vicor filter (200 W). While the exterior of the reactor was cooled with ice, the inside atmosphere of the reactor was replaced by an argon gas, and the solution was exposed to ultraviolet irradiation for 1.5 minutes. At this time, the inside temperature reached 14° C.

After the reaction, the reaction mixture was transferred to an eggplant-shaped flask, and refluxed for 2 hours in an atmosphere of argon.

Then, the solvent was distilled off. The residue was chromatographed on a thin layer of silica gel impregnated with silver nitrate using a benzene/acetone (40/1) developing solvent to afford 552 μg of a purified product having the following characteristics.

UV ($\lambda_{max}^{ethanol}$, nm): 264, 245 (shoulder).

NMR (CDCl$_3$, δ(ppm)): 0.55 (3H, s, 18-CH$_3$), 1.60 and 1.67 (6H, bs, 26,27-(CH$_3$)$_2$), 2.03 and 2.06 (6H, a pair of s, 1,3-(CH$_3$CO)$_2$), 4.8–5.6 (3H, m, 1β,3α,24-H$_3$), 5.04 and 5.31 (2H, a pair of bs, 19-CH$_2$), 5.90 and 6.35 (2H, a pair of d, J=11Hz, 6.7-H$_2$).

Mass (m/e): 482 (M$^+$), 422 (M$^+$-CH$_3$COOH), 380, 362 (M$^+$-2CH$_3$COOH).

High resolution mass spectrum: Found=482.3390. Require, M$^+$(C$_{31}$H$_{46}$O$_4$)=482.3396.

From the above characteristics, this product was identified as 1α-hydroxy-24-dehydrovitamin D$_3$ diacetate.

EXAMPLE 4

Preparation of 1α-OH-Δ$^{24}$-D$_3$ from 1α-OH-Δ$^{24}$-D$_3$ dibenzoate:

1.5 mg of 1α-hydroxy-24-dehydrovitamin D$_3$ dibenzoate was stirred together with 5 ml of a 5% methanol solution of potassium hydroxide, and the mixture was allowed to stand overnight at 40° C.

The methanol was distilled off, and water was added. The mixture was extracted with ethyl ether. The ether layer separated was washed successively with dilute hydrochloric acid, a saturated aqueous solution of sodium carbonate, and water, and dried with anhydrous sodium sulfate. The solvent was distilled off.

The resulting residue was chromatographed on a thin layer of silica gel impregnated with silver nitrate using a benzene/acetone (5/1) developing solvent to separate 0.8 mg of a purified product which was identified as 1α-hydroxy-24-dehydrovitamin $D_3$ obtained in the other Examples.

EXAMPLE 5

Preparation of 1α-OH-$\Delta^{24}$-pre $D_3$ by step 3:

10 mg of 1α,3β-dihydroxycholesta-5,7,24-triene was dissolved in a mixture of 100 ml of benzene and 40 ml of ethyl alcohol.

The solution was placed in an ordinary photoreaction apparatus consisting of a reactor having a lamp provided at its center. The lamp used was a medium-pressure mercury lamp equipped with a Vicor filter (200 W). While the exterior of the reactor was cooled with ice, the inside atmosphere of the reactor was replaced by an argon gas, and the solution was exposed to ultraviolet irradiation for 2.5 minutes. At this time, the inside temperature reached 14° C.

After the reaction, the solvent was distilled off at 20° C. under reduced pressure. The resulting residue was chromatographed on a thin layer of silica gel impregnated with silver nitrate using a benzene/acetone (5/1) developing solvent. The spots were scraped off and eluted with methylene chloride. The solvent was distilled off at 20° C. under reduced pressure to afford 1.8 mg of a purified product which was directly used as a sample for characterization. It showed the following characteristics. NMR spectra were measured at −20° C.

UV ($\lambda_{max}^{ethanol}$, nm) 258.

NMR (CDCl$_3$, δ(ppm)): 0.69 (3H, s, 18-CH$_3$), 1.60, 1.67 (6H, a pair of bs, 26-, 27-(CH$_3$)$_2$), 1.78 (3H, bs, 19-CH$_3$), 4.05 (1H, m, 3α-H), 4.21 (1H, m, 1β-H), 5.09 (1H, bt, J=7Hz, 24-H), 5.50 (1H, m, 9H), 5.77, 5.95 (2H, a pair of d, J=12Hz, 6-,7-H$_2$).

Mass (m/e): 398 (M$^+$), 380 (M$^+$-H$_2$O), 362 (M$^+$-2H$_2$O).

High resolution mass spectrum: Found=398.3198. Require, M$^+$(C$_{27}$H$_{42}$O$_2$)=398.3185.

From the above characteristics, the resulting product was identified as 1α-hydroxy-24-dehydroprevitamin $D_3$.

EXAMPLE 6

Preparation of 1α-OH-$\Delta^{24}$-pre $D_3$ diacetate by step 3:

The reaction of Example 5 was repeated except that 20 mg of 1α,3β-diacetoxycholesta-5,7,24-triene was used instead of 10 mg of 1α,3β-dihydroxycholesta-5,7,24-triene.

After the reaction, the reaction product was purified in the same way as in Example 5 except that benzeneacetone (40:1) was used as the developing solvent for chromatography. Thus, 3.2 mg of a purified product was obtained.

The purified product showed the following characteristics. NMR spectra were measured at −20° C.

UV ($\lambda_{max}^{ethanol}$, nm): 258.

NMR (CDCl$_3$, δ(ppm)): 0.67 (3H, s, 18-CH$_3$), 1.60 (3H, bs, 26-CH$_3$), 1.66 (6H, bs, 19-,27-(CH$_3$)$_2$), 2.06, 2.11 (6H, a pair of s, 1-,3-(CH$_3$COO)$_2$), 5.07 (2H, m, 3α-,24-H$_2$), 5.46 (2H, m, 1β-,9-H$_2$), 5.79, 5.95 (2H, a pair of d, J=12Hz, 6-,7-H$_2$).

Mass (m/e): 482 (M$^+$), 422 (M$^+$-CH$_3$COOH), 380, 362 (M$^+$-2CH$_3$COOH),

High resolution mass spectrum: Found=482.3386. Require, M$^+$(C$_{31}$H$_{46}$O$_4$)=482.3396.

From the above characteristics the product was identified as 1α-hydroxy-24-dehydroprevitamin $D_3$ diacetate.

EXAMPLE 7

Preparation of 5,7,24-triene by step 2:

15 mg of 1α,3β-diacetoxy-24-dehydrocholesta-5,7-diene obtained by the same method as in Example 1 was dissolved in 10 ml of a 5% methanol solution of potassium hydroxide. The solution was allowed to stand overnight at room temperature with stirring. The reaction solvent was distilled off under reduced pressure, and water and ethyl acetate were added. The mixture was shaken in a separatory funnel, and the organic layer was separated. The remaining aqueous layer was shaken twice with ethyl acetate, and the organic layers were separated. These organic layers were combined, washed successively with 1N hydrochloric acid, a saturated aqueous solution of sodium hydrogen carbonate and water, and then dried over sodium sulfate. The solvent was distilled off under reduced pressure to afford 15 mg of a residue.

The residue was chromatographed on a thin layer of silica gel with benzene-acetone (5:1) as a developing solvent to afford 10 mg of a product having the following characteristics.

UV ($\lambda_{max}^{ethanol}$, nm): 261, 271, 282, 293.

NMR (CDCl$_3$, δ(ppm)): 0.63 (3H, s, 18-CH$_3$), 0.95 (3H, s, 19-CH$_3$), 1.60 1.67 (6H, a pair of bs, 26-,27-(CH$_3$($_2$), 3.7 (1H, bs, 1β-H), 4.1 (1H, m, 3α-H), 5.08 (1H, bt, J=7Hz, 24-H), 5.38, 5.72 (2H, a pair of m, 6-,7-H$_2$).

Mass (m/e): 398 (M$^+$), 380 (M$^+$-H$_2$0), 362 (M$^+$-2H$_2$O).

From the above characteristics, the resulting product was identified as 1α,3β-dihydroxy-24-dehydrocholesta-5,7-diene.

EXAMPLE 8

Preparation of 5,7,24-triene by steps 1 and 2:

The reaction and purification of Example 1 were repeated except that 20 mg of 24-hydroxy-1α,3β-di(tetrahydropyranyloxy)cholesta-5,7-diene was used instead of 20 mg of 1α,3β-diacetoxy-24-hydroxycholesta-5,7-diene. Thus, 6 mg of a product having the following characteristics was obtained.

UV ($\lambda_{max}^{ethanol}$, nm): 261, 271, 282, 293.

NMR (CDCl$_3$, δ(ppm)): 0.62 (3H, s, 18-CH$_3$). 0.94 (3H, bs, 19-CH$_3$), 1.60, 1.67 (6H, a pair of bs, 26-,27-(CH$_3$)$_2$), 3.2–4.1 (6H, m, 1β-,3α-H$_2$ & 2(H$_2$) at the 6-position of tetrahydropyranyl), 4.73 (2H, m, 2(H) at the 2-position of tetrahydropyranyl), 5.09 (1H, bt, J=7Hz, 24-H), 5.35, 5.63 (2H, a pair of m, 6-,7-H$_2$).

From the above characteristics, the resulting product was identified as 1α,3β-di(tetrahydropyranyloxy)-24-dehydrocholesta-5,7-diene.

EXAMPLE 9

Preparation of 5,7,24-triene by steps 1 and 2:

The reaction of Example 1 was repeated except that 20 mg of 1α,3β-dibenzoyloxy-24-hydroxycholesta-5,7-diene was used instead of 20 mg of 1α,3β-diacetoxy-24-hydroxycholesta-5,7-diene. The reaction product was purified in the same way as in Example 1 except that the developing solvent for chromatography was changed benzene/hexane (2:1). Thus, 6 mg of a product having the following characteristics was obtained.

UV ($\lambda_{max}^{ethanol}$, nm): 231, 261, 271, 282, 293.

NMR (CDCl$_3$, δ(ppm)): 1.60, 1.67 (6H, a pair of s, 26-,27-(CH$_3$)$_2$), 4.95 (1H, m, 3α-H), 5.09 (1H, m, 24-H), 5.32 (2H, m, 1β-H & 6- or 7-H), 5.72 (1H, m, 6- or 7-H), 7.49, 8.02 (10 H, m, aromatic-2(H$_5$)).

Mass (m/e): 606 (M+), 484 (M+-benzoic acid), 362 (M+-2-benzoic acid).

From the above characteristics, the product was identified as 1α,3β-dibenzoyloxy-24-dehydrocholesta-5,7-diene.

EXAMPLE 10

Preparation of 5,7,24-triene by steps 1 and 2:

The reaction and purification of Example 1 were repeated except that 20 mg of 24-hydroxy-1α,3β-dipivaloyloxy-cholesta-5,7-diene was used instead of 20 mg of 1α,3β-diacetoxy-24-hydroxycholesta-5,7-diene. Thus, 7 mg of a product having the following characteristics was obtained.

UV ($\lambda_{max}^{ethanol}$, nm): 261, 271, 282, 293.

NMR (CDCl$_3$, δ(ppm): 0.61 (3H, s, 18-CH$_3$), 1.16 (9H, s, 3-position pivaloyl-(CH$_3$)$_3$), 1.22 (9H, s, 1-position pivaloyl-(CH$_3$)$_3$), 1.60, 1.67 (6H, a pair of bs, 26-,27-(CH$_3$)$_2$), 4.92 (2H, m, 1β-, 3α-H$_2$), 5.09 (1H, bt, J=7Hz, 24-H), 5.36, 5.64 (2H, a pair of m, 6-,7-H$_2$).

From the above characteristics, the resulting product was identified as 1α,3β-dipinaloyloxy-24-dehydrocholesta-5,7-diene.

EXAMPLE 11

Preparation of 5,7,24-triene by steps 1 and 2:

10 mg of 1α,3β-dihydroxy-24-dehydrocholesta-5,7-diene prepared in the same way as in Example 7 was dissolved in 1 ml of N-trimethylsilylimidazole. The solution was allowed to stand overnight.

Then, 20 ml of n-hexane and 10 ml of water were added, and the mixture was shaken by a separatory funnel. The organic layer was separated. The remaining aqueous layer was shaken twice with 10 ml of n-hexane, and the organic layers were separated. These organic layers were combined, washed twice with 20 ml of water, and dried over sodium sulfate. The solvent was distilled off under reduced pressure to afford 11 mg of a residue.

The residue was chromatographed on a thin layer of silica gel with benzene/hexane (1:2) as a developing solvent to afford 6 mg of a product having the following characteristics.

UV ($\lambda_{max}^{ethanol}$, nm): 261, 271, 282, 293

NMR (CDCl$_3$, δ(ppm)): 0.13 (18H, s, trimethylsilyl-2(CH$_3$)$_3$), 0.62 (3H, s, 18-CH$_3$), 0.90 (3H, s, 19-CH$_3$), 1.60, 1.67 (6H, a pair of bs, 26-,27-(CH$_3$)$_2$), 3.74 (1H, m, 1β-H), 4.02 (1H, m, 3α-H), 5.09 (1H, bt, J=7Hz, 24-H), 5.34, 5.65 (2H, a pair of m, 6-,7-H$_2$).

Mass (m/e): 542 (M+), 452 (M+-trimethylsilanol), 362 (M+-2 trimethylsilanol).

From the above characteristics, the resulting product was identified as 1α,3β-di(trimethylsilyloxy)-24-dehydrocholesta-5,7-diene.

EXAMPLE 12

Preparation of 1α-OH-Δ$\overset{=}{}$-pre D$_3$ by step 3:

In the same way as in Example 5, 1α,3β-di(tetrahydropyranyloxy)-24-dehydrocholesta-5,7-diene, 1α,3β-dibenzoyloxy-24-dehydrocholesta-5,7-diene, 1α,3β-dipivaloyloxy-24-dehydrocholesta-5,7-diene, and 1α,3β-di(trimethylsilyloxy)-24-dehydrocholesta-5,7-diene were each irradiated and chromatographed to afford the corresponding 1α-hydroxy-24-dehydroprevitamin D$_3$-di(tetrahydropyranyl ether), -dibenzyl ester, -dipivaloyl ester, and -di(trimethylsilyl ether). These products were identified by UV spectra, and NMR spectra measured at −20° C.

EXAMPLE 13

Preparation of 1α-OH-Δ$^{24}$-D$_3$ by steps 3 and 4:

20 mg of 1α,3β-di(trimethylsilyloxy)-24-dehydrocholesta-5,7-diene was irradiated, isomerized and post-treated in the same way as in Example 2. The product was purified in the same way as in Example 2 except that benzene/hexane (1:2) was used as a developing solvent for chromatography. Thus, 2.6 mg of a product having the following characteristics was obtained.

UV ($\lambda_{max}^{ethanol}$, nm): 264.

NMR (CDCl$_3$, δ(ppm):
0.12 (18H, s, trimethylsilyl 2(CH$_3$)$_3$),
0.54 (3H, s, 18-CH$_3$),
1.60, 1.68 (6H, a pair of bs, 26-27-(CH$_3$)$_2$),
4.0–4.5 (2H, m, 1β-3α-H$_2$),
4,89, 5.17 (2H, a pair of bs, 19-CH$_2$),
5.09 (1H, bt, J=7Hz, 24-H,
6.01, 6.27 (2H, a pair of d, J=12Hz, 6-,7-H$_2$).
Mass (m/e): 542 (M+), 452 (M+-trimethylsilanol), 362 (M+-2 trimethylsilanol).

From the above characteristics, the resulting product was identified as 1α-hydroxy-24-dehydrovitamin D$_3$ di (trimethylsilyl ether).

EXAMPLE 14

Preparation of 1α-OH-Δ$^{24}$-D$_3$ derivatives by steps 3 and 4:

In the same way as in Example 3, 1α,3β-di(tetrahydropyranyloxy)-24-dehydrocholesta-5,7-diene, 1α,3β-dibenzoyloxy-24-dehydrocholesta-5,7-diene, and 1α,3β-dipivaloyloxy-24-dehydrocholesta-5,7-diene were each irradiated, isomerized and chromatographed to afford the corresponding 1α-hydroxy-24-dehydrovitamin D$_3$-di(tetrahydropyranyl ether), -dibenzoyl ester, and -dipivaloyl ester. These products were identified by U. V. spectra and NMR spectra.

EXAMPLE 15

1α-hydroxy-24-dehydrovitamin D$_3$ was dissolved in coconut oil. The amount of the 1α-hydroxy-24-dehydrovitamin D$_3$ was 0.6 mg per 100 g of the coconut oil. Transparent soft capsules containing 150 mg of the resulting solution per capsule were produced in a customary manner by means of a soft-capsule making machine.

EXAMPLE 16

Effect of 1α-hydroxy-24-dehydrovitamin D$_3$(1α-OH-Δ$^{24}$-D$_3$) to promote calcium absorption from the intestinal tract:

Comparison with 1α-hydroxyvitamin D$_3$ (1α-OH-D$_3$)

Weanling Wistar male rats (with a body weight of about 100 g) which had been fed only with vitamin D-deficient diet for 6 weeks were fasted overnight. A solution of 1α-OH-Δ$^{24}$-D$_3$(250 pmols) in a 1:1 mixture of ethanol and physiological saline solution or a solution of 1α-OH-D$_3$ (250 pmols) in the same mixture in a concentration of 250 pmoles was intravenously administered to the rats. They were killed 14 hours later, and calcium absorption at the intestinal tube was measured by the everted gut sac method [see Martin, D. L. and DeLuca, H. F., Amer. J. Physiol. 216, 1351 (1969)]. Rats in a control group were administered with 200 μl of a 1:1 mixture of ethanol and physiological saline solution. The radioactivity level was determined by placing 0.2 ml of an incubation medium in a vial, adding 12 ml of a cocktail containing a scintillator (containing 600 ml of toluene, 400 ml of ethyl Cellosolve, 4 g of DPO and 150 mg of POPOP), and measuring the radioactivity by a liquid scintillation counter.

The results are shown in Table 1.

POP above stands for 2,5-diphenyloxazole, and POPOP, for 2,2'-p-phenylene bis (5-phenyloxazole).

|  | $^{45}$Ca (S/M) |
|---|---|
| Control | 1.98 ± 0.21 (3)* |
| 1α-OH-Δ$^{24}$-D$_3$ (250) p moles) | 3.97 ± 0.26$^a$ (3)* |
| 1α-OH—D$_3$ (250 p moles) | 4.08 ± 0.05$^a$ (3)* |

*The numbers in the parentheses show the number of rats in a particular group
$^a$P <1.01

The experimental conditions were as follows:
Intestinal tract used: duodenum, 7 cm
Amount of the medium poured in the everted duodenum: 0.6 ml
Composition of the medium:

| NaCl | 125 mM |
|---|---|
| Fructose | 10 mM |
| Tris-HCl buffer (pH 7.4) | 30 mM |
| CaCl$_2$ | 0.25 mM |
| $^{45}$CaCl$_2$ | 10 μCi/l |

Incubating conditions: 37° C., 90 minutes; a gaseous mixture of 95% O$_2$ and 5% CO$_2$ was passed.
Amount of the medium used for the measurement of radioactivity: 0.2 ml It is seen from the experimental results that 1α-OH-Δ$^≃$-D$_3$ has an equivalent effect of promoting intestinal calcium absorption to 1α-OH-D$_3$.

EXAMPLE 17

Effect of 1α-OH-Δ$^{24}$-D$_3$ to increase the serum calcium and the serum phosphoric acid:
Comparison with 1α-OH-D$_3$ Weanling Wistar male rats (with a body weight of about 100 g) which has been fed with vitamin D-deficient diet for 6 weeks were fasted overnight, and then a solution of 1α-OH-Δ$^{24}$-D$_3$ (250 pmols or 1250 pmols) dissolved in a 1:1 mixture of ethanol and physiological saline solution, or a solution of 1α-OH-D$_3$ (250 pmols) in the same mixture was intravenously administered to the rats. They were killed 14 hours later, and the calcium and phosphoric acid levels in the serum were determined. A calcium determining kit and a phosphorus determining kit (products of Iatron Company) were used. The results are shown in Table 2.

TABLE 2

|  | Serum Ca (mg/dl) | Serum PO$_4$ (mg/dl) |
|---|---|---|
| Control | 4.66 ± 0.07 (3)* | 5.31 ± 0.29 (3)* |
| 1α-OH-Δ$^{24}$-D$_3$ (250 p moles) | 5.02 ± 0.19 (3)* | 5.22 ± 0.04 (3)* |
| 1α-OH-Δ$^{24}$-D$_3$ (1250 p moles) | 5.23 ± 0.09 $^a$ (3)* | 5.26 ± 0.08 (3)* |

TABLE 2-continued

|  | Serum Ca (mg/dl) | Serum PO$_4$ (mg/dl) |
|---|---|---|
| 1α-OH—D$_3$ (250 p moles) | 5.56 ± 0.07$^b$ (3)* | 5.25 ± 0.41 (3)* |

*The numbers in the parentheses show the number of rats in a particular group.
$^a$P<0.05
$^b$P <0.01

Since in this experiment, the rats were fed with a feed substantially free from calcium are were fasted prior to the test, there was substantially no calcium absorption from the intestinal tract. Hence, a rise in serum calcium level is believed to be the result of dissolution from the bone tissues (bone resorption activity). It is seen from the experimental results that 1α-OH-Δ$^≃$-D$_3$ has a weaker bone resorption activity than 1α-hydroxyvitamin D$_3$. This means that the 1α-OH-Δ$^≃$-D$_3$ in accordance with this invention has the property or selectively promoting calcium absorption from the intestinal tract and has a weaker bone resorbing activity than the known active type of vitamin D$_3$ analog. Accordingly, this compound of the invention will be very useful as a medicine with reduced side-effects in application to various diseases caused by abnormal metabolism of calcium and is expected to be used successfully for the treatment of a wide range of diseases caused by abnormal metabolism of calcium.

What we claim is:

1. 1α-Hydroxy-24-dehydrovitamin D$_3$ or its derivatives having a protected hydroxyl group of the formula

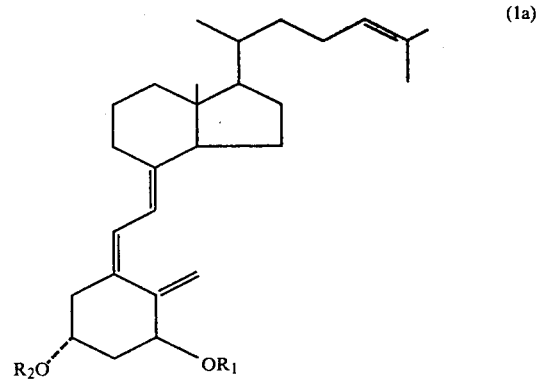

(Ia)

wherein R$_1$ and R$_2$ are identical or different, and each represents a hydrogen atom, a carboxylic acid residue or a group which forms an ether linkage with a hydroxyl group.

2. 1α-Hydroxy-24-dehydrovitamin D$_3$ of the following formula

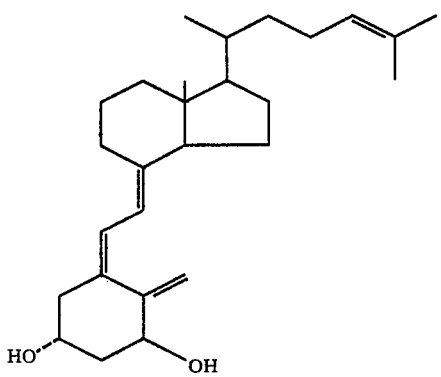

[Ia]

3. A pharmaceutical composition for enhancing the calcium absorption from the intestinal tract or the calcium bone resorption of warm-blooded animals comprising a therapeutically effective amount of 1α-hydroxy-24-dehydrovitamin $D_3$ of the formula

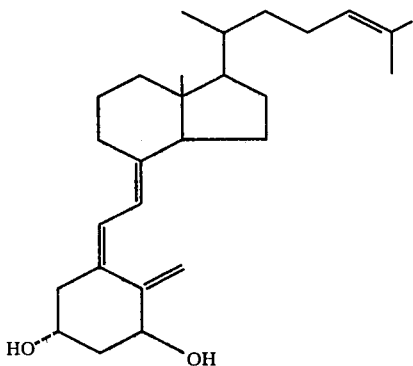

(Ia)

4. A pharmaceutical composition for warm-blooded animals according to claim 3 which is administrable orally or by intramuscular or intravenous injection, said composition comprising a pharmaceutically effective amount of 1α-hydroxy-24-dehydrovitamin $D_3$.

5. A method for enhancing the calcium absorption from the intestinal tract or the calcium bore resorption of warm-blooded animals, which comprises administering orally, buccally or parenterally a therapeutically effective amount of 1α-hydroxy-24-dehydrovitamin $D_3$ of the following formula

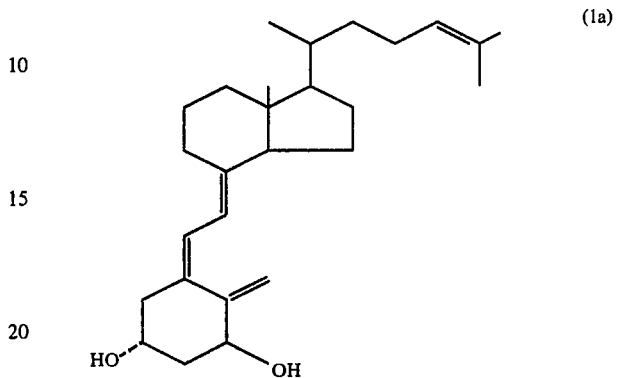

said therapeutically effective amount being 0.01 to 10 μg daily per kilogram of body weight of the warm-blooded animal.

6. A method for enhancing the calcium absorption from the intestinal tract or the calcium bone resorption of man according to claim 5, which comprises administering to a human said therapeutically effective amount of 1α-hydroxy-24-dehydrovitamin $D_3$ orally, subcutaneously, intramuscularly or intravenously.

7. A method for treating vitamin D resistant hypocalcemia and bone diseases selected from the group consisting of vitamin D-dependent rickets, renal osteodystrophy, hypoparathyroidism, osteoporosis, osteomalacia, Behcet disease, malabsorption syndrome, hypocalcemia induced by liver cirrbosis, hypocalcemia induced by steatorrhoea, hypocalcemia caused by vitamin D-resistant rickets, which comprises administering 1α-hydroxy-24-dehydrovitamin $D_3$ to a patient in a dosage of 0.01 to 10 μg per kilogram of body weight daily either orally, subcutaneously, intramuscularly or intravenously.

* * * * *